United States Patent [19]

Yasuo et al.

[11] 4,415,569

[45] Nov. 15, 1983

[54] PYRAZOLOINDAZOLE DERIVATIVES AND PHARMACEUTICAL COMPOSITION CONTAINING THE SAME

[75] Inventors: Fujimura Yasuo, Saitama; Tanaka Sadao; Matsunaga Isao, both of Tokyo; Yasuyuki Shiraki, Tokyo; Yugo Ikeda, Sayama; Tamotsu Yamazaki, Tokorozawa; Yasuhiro Ohba, Kawasaki; Kazushige Sakai, Tokyo; Shun-ichi Hata, Yokohama; Minoru Shindo, Tokyo, all of Japan

[73] Assignee: Chugai Seiyaku Kabushiki Kaisha, Tokyo, Japan

[21] Appl. No.: 331,896

[22] Filed: Dec. 17, 1981

[30] Foreign Application Priority Data

Dec. 26, 1980 [JP] Japan ................... 55-184106

[51] Int. Cl.³ ............... A61K 31/415; C07D 487/04
[52] U.S. Cl. ............... 424/248.57; 424/250; 424/267; 424/273 N; 544/140; 544/371; 546/199; 548/371
[58] Field of Search ............... 548/371; 544/140, 371; 546/199; 424/273 N, 248.57, 250, 267

[56] References Cited

FOREIGN PATENT DOCUMENTS

23633A1 2/1981 European Pat. Off. .

OTHER PUBLICATIONS

Elguero et al., Bull. Soc. Chim. France 1969, No. 6, pp. 2064–2076.

Fujimura et al., Chem. Abst. 1981, vol. 95, No. 80949r.

*Primary Examiner*—Richard Raymond
*Attorney, Agent, or Firm*—Browdy and Neimark

[57] ABSTRACT

Pyrazoloindazole derivatives of the formula:

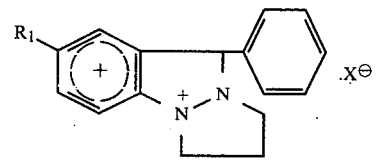

[wherein $R_1$ is a cyano group, carboxy group, a lower alkoxycarbonyl group or a group

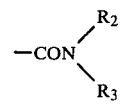

(wherein $R_2$ and $R_3$ are each a hydrogen atom, a lower alkyl group, a phenyl group which may have a substituent or when taken together with a nitrogen atom, form a heterocyclic ring); $X^\ominus$ is a counter ion], a process for preparing the same and a pharamaceutical composition containing the same are disclosed. The compounds of the formula above have bronchodilating action and are useful as a medicine.

10 Claims, No Drawings

PYRAZOLOINDAZOLE DERIVATIVES AND PHARMACEUTICAL COMPOSITION CONTAINING THE SAME

The present invention relates to pyrazoloindazole derivatives of the formula:

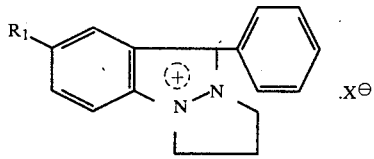
(I)

[wherein $R_1$ is a cyano group, carboxy group, a lower alkoxycarbonyl group or a group

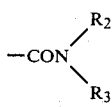

(wherein $R_2$ and $R_3$ are each a hydrogen atom, a lower alkyl group, a phenyl group which may have a substituent or when taken together with a nitrogen atom, form a heterocyclic ring; $X^\ominus$ is a counter ion].

The lower alkoxycarbonyl group as a definition of $R_1$ in the formula (I) is an alkoxycarbonyl group having 2 to 5 carbon atoms, such as methoxycarbonyl, ethoxycarbonyl, n-propoxycarbonyl, n-butyloxycarbonyl or isobutyloxycarbonyl. The lower alkyl group as a definition of $R_2$ and $R_3$ is an alkyl group having 1 to 4 carbon atoms, such as methyl, ethyl, n-propyl, isopropyl, n-butyl, isobutyl, sec-butyl, or tert-butyl. Examples of the heterocyclic ring formed by $R_2$ and $R_3$ when they are taken together with a nitrogen atom are piperidino, piperazino, pyrrolidino and morpholino. The substituent on the phenyl group for $R_2$ or $R_3$ is a lower alkyl group having 1 to 4 carbon atoms. Examples of the counter ion as the definition of $X^\ominus$ are a halide ion, hydroxide ion, methanesulfonate ion, p-toluenesulfonate ion, sulfate ion, nitrate ion, carbonate ion, acetate ion, benzoate ion and salicylate ion.

One method of producing the compound of the formula (I) is as follows: a compound of the formula (II):

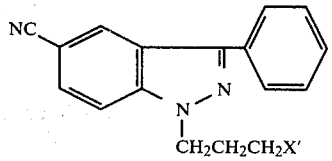
(II)

(wherein X' is a halogen atom) is cyclized under heating to form a compound of the formula (III):

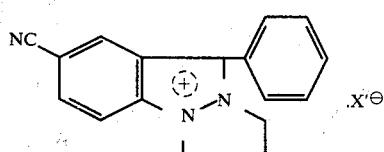
(III)

(wherein X' is the same as defined above); the compound (III) is hydrolyzed into a compound (IV):

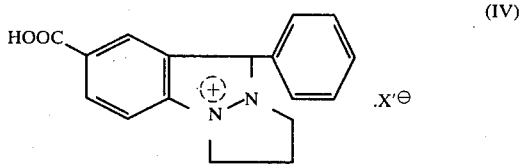
(IV)

(wherein X' is the same as defined above); the compound (IV) or is reacted with (1) lower alkanol or (2) a compound of the formula (V):

(wherein $R_2$ and $R_3$ are the same as defined above). If necessary, the counter ion of the compound prepared can be exchanged with other species of ion through, for example, ion exchange resin treatment.

The counter ion in the compound (I) that derives from the compound (II) can be converted into another anion by treatment with an ion-exchange resin; examples of the anion are a halide ion, hydroxide ion, methanesulfonate ion, p-toluenesulfonate ion, sulfate ion, nitrate ion, carbonate ion, acetate ion, benzoate ion and salicylate ion.

The compound (II) can easily be prepared by reacting 1,3-dihalogenopropane with 5-cyano-3-phenylindazole in the presence of sodium hydride. The 5-cyano-3-phenylindazole is derived from 5-formyl-3-phenylindazole.

The cyclization reaction progresses by merely heating the compound (II) in the presence of or in the absence of a solvent. The heating is usually effected at 50° to 150° C. The solvent which may be used in the cyclization reaction is acetone, benzene, toluene, xylene or the like. The use of a solvent makes the reaction easy to control and separation of the product after completion of the reaction can be done by a simple process for example, by filtration.

Hydrolyzation of the compound (III) is carried out by heating the compound in an aqueous solvent in the presence of an acid. The heating is usually effected at 80° C. to 120° C. Acids which may be used for this reaction are, for example, hydrochloric acid, sulfuric acid or hydrobromic acid.

Esterification of the compound (IV) is carried out by heating the mixture of the compound (IV) and a lower alkanol in the presence of an acid catalyst, for example, hydrochloric acid or sulfuric acid. The heating is usually effected at 30° C. to 120° C. Furthermore, the esterification can be carried out also by allowing a mixture of the halide of the compound (IV) and a lower alkanol to stand at room temperature.

The reactive of the compound (IV) with the compound (V) is carried out by condensing the compound of the formula (V) with a reaction derivative of the compound represented by the formula (IV) at a temperature of from usually −10° to 100° C., preferably 0° to 50° C. for 0.5-4 hours. A solvent which is used for this reaction is, for example, benzene, toluene, tetrahydrofuran, diethylether, dioxane, dimethylformamide, chloroform, methylene chloride, acetonitrile, acetone, carbon tetrachloride, ethyl acetate or the like. Accelerators for the condensation reaction of this invention include, for example, inorganic bases such as hydroxides, acetates and carbonates of an alkali metal or alkaline earth metal, for example, potassium acetate, sodium acetate, sodium carbonate, potassium carbonate, sodium hydroxide, calcium acetate and calcium carbonate; and tertiary amine organic bases, for example, pyridine, triethylamine, dimethylaniline and picoline. The reactive derivatives of compound (IV) include; acid halides such as acid chloride; acid anhydride; mixed acid anhydrides.

Furthermore, a compound of the formula (IV) can be reacted with a compound of the formula (V) in an inert solvent at a temperature of from room temperature to reflux temperature of the solvent used for 1–5 hours in the presence of an amide formation accelerator such as an imide compound, e.g., N,N'-dicyclohexylcarbodiimide, N-cyclohexyl-N'-morpholinoethylcarbodiimide or N,N'-diethylcarbodiimide; an imine compound, e.g., diphenylketene-N-cyclohexylimine or pentamethyleneketene-N-cyclohexylimine. Inert solvents which may be used in this reaction include, for example, benzene, toluene, tetrahydrofuran, chloroform, dioxane, acetonitrile, dimethylformamide and the like.

The compounds of the present invention thus produced have bronchodilating action and are useful as a medicine.

EXPERIMENT

According to the method of Himori et al. (Br. J. Pharmac. (1976), 56, 293–299), a tracheal tube with a cuff was inserted into the trachea of a dog and the change of pressure on the cuff was measured by a pressure transducer connected to the cuff to thereby determine the effect of the test compounds on dilatation of the tracheal muscles. Each of the test compounds and controls listed in Table 1 was dissolved in physiological saline and administered intravenously in a dose of 1 mg/kg. The results are shown in the Table.

TABLE

| Test compound | Intraluminal pressure | | |
|---|---|---|---|
| | % change | prolonged time | Ratio[1] |
| Compound of Example 1 | 100% | 12 min | 4.44 |
| Compound of Example 2 | 100% | 12 min | 4.44 |
| Compound of Example 3 | 30% | 5 min | 0.56 |
| noradrenaline[2] | 90% | 3 min | 1.00 |

[1]The ratio was calculated as a value relative to the max. % change × prolonged time for Noradrenaline that was assumed to be 1.00.
[2]Administered in a dose of 1 μg/kg

EXAMPLE 1

A mixture of 22 g of 5-formyl-3-phenylindazole, 8 g of hydroxylamine hydrochloride and 12.5 g of sodium formate was added to 150 ml of formic acid, and after refluxing for 2 hours, the mixture was extracted with chloroform. The extract was washed with water, dried over anhydrous sodium sulfate and concentrated to give 16.5 g of 5-cyano-3-phenylindazole (m.p. 150°–151° C.).

To a solution of 4.2 g of the 5-cyano-3-phenylindazole in 20 ml of dimethylformamide, 0.8 g of 60% sodium hydride was added, and the mixture was stirred for 10 minutes. The mixture was added dropwise to a mixture of 7 ml of 1,3-dibromopropane and 10 ml of dimethylformamide under cooling with ice. The mixture was stirred for 10 minutes at room temperature and extracted with benzene. The extract was washed with water, dried over anhydrous sodium sulfate and concentrated. The residue was subjected to column chromatography on silica gel to produce 3.5 g of 1-(3'-bromopropyl)-5-cyano-3-phenylindazole (recrystallization from ethanol provided a m.p. of 100° to 102° C.).

When 3 g of the 1-(3'-bromopropyl)-5-cyano-3-phenylindazole was heated in an oilbath at 120° C., the product melted first, then crystallized. After the crystallized product was heated for 10 minutes, the crystal was recovered and washed with benzene to produce 2.4 g of 2,3-dihydro-7-cyano-9-phenyl-1H-pyrazolo[1,2-a]indazolium bromide. Recrystallization from water provided a m.p. of 234° C. (with decomposition).

Elemental analysis: Calculated $C_{17}H_{14}N_3Br$: C 60.02, H 4.15, N 12.35 (%). Found: C 59.69, H 4.06, N 12.28 (%).

EXAMPLE 2

Two grams of the 2,3-dihydro-7-cyano-9-phenyl-1H-pyrazolo[1,2-a]indazolium bromide produced in Example 1 was dissolved in 20 ml of 6N hydrochloric acid, and the solution was refluxed for 6 hours. The refluxed mixture was cooled to room temperature and the resulting crystal was filtered to provide 1.7 g of a mixture of 2,3-dihydro-7-carboxy-9-phenyl-1H-pyrazolo[1,2-a]indazolium bromide and chloride. The mixture was purified with a bromo type ion-exchange resin IRA-401 to provide 1,3 g of 2,3-dihydro-7-carboxy-9-phenyl-1H-pyrazolo[1,2-a]indazolium bromide. Recrystallization from hydrous methanol provided a m.p. of at least 300° C.

Elemental analysis: Calculated $C_{17}H_{15}N_2O_2Br$: C 56.84, H 4.21, N, 7.80 (%). Found: C 56.73, H 4.19, N, 7.74 (%).

EXAMPLE 3

The 2,3-dihydro-7-carboxy-9-phenyl-1H-pyrazolo[1,2-a]indazolium bromide (3.8 g) produced in Example 2 was dissolved in 50 ml of ethanol-hydrochloric acid, and the solution was refluxed for one hour and concentrated to produce 4 g of a mixture of 2,3-dihydro-7-ethoxycarbonyl-9-phenyl-1H-pyrazolo[1,2-a]indazolium bromide and chloride. The product was purified with a bromo type ion-exchange resin IRA-401 to provide 3.2 g of 2,3-dihydro-7-ethoxycarbonyl-9-phenyl-1H-pyrazolo[1,2-a]indazolium bromide. Recrystallization from water provided a m.p. of 212°–214° C. (with decomposition).

Elemental analysis: Calculated $C_{19}H_{19}N_2O_2Br \cdot \frac{1}{4} H_2O$: C 57.59, H 5.09, N 7.07 (%). Found: C 57.34, H 5.01, N 6.86 (%).

EXAMPLE 4

The mixture of 2 g of 2,3-dihydro-7-carboxy-9-phenyl-1H-pyrazolo[1,2-a]indazolium chloride and 30 ml of thionyl chloride was heated at 50° C. for 30 minutes with stirring, and the resulting reaction mixture was concentrated to give residue. A suspension of the residue in 50 ml of chloroform and 15 ml of isobutanol was stirred at room temperature for an hour. Then the mixture was concentrated under reduced pressure to give an oily residue, which was suspended in ethyl ether. The suspension was filtered to produce 2.1 g of 2,3-dihydro-7-isobutyloxycarbonyl-9-phenyl-1H-pyrazoro[1,2-a]indazolium chloride as a powder. m.p. 130°–132° C. Mass spectrum absorption (m/e) 84, 86, 251, 307, 370 (parent peak).

EXAMPLE 5

The mixture of 2 g of 2,3-dihydro-7-carboxy-9-phenyl-1H-pyrazolo[1,2-a]indazolium chloride and 30 ml of thionyl chloride was heated at 50° C. for 30 minutes with stirring, and the resulting reaction mixture was concentrated to produce residue. The mixture of the above residue, 50 ml of chloroform and 5 ml of morpholine was stirred at room temperature for 30 minutes, and then the mixture was filtered. The filtrate was concentrated to produce an oily product, which was purified by column chromatography on HP-2MG ® (Mitsubishi Chemical Industries Limited) using water as an eluent to produce 1.5 g of 2,3-dihydro-7-morpholino carbonyl-9-phenyl-1H-pyrazolo[1,2-a]indazolium chloride as an oily substance.

Mass spectrum absorption (m/e) 86, 100, 115, 297, 383 (parent peak).

EXAMPLES 6 and 7

The compounds indicated below were prepared as in Example 5.

| Ex. No. | Compound | Melting Point | Mass Spectrum Absorption (m/e) |
|---|---|---|---|
| 6 | 2,3-Dihydro-7-[(4-methylanilino)carbonyl]-9-phenyl-1H—pyrazolo[1,2-a]indazolium chloride | 192–194° C. | 297, 403 (parent peak) |
| 7 | 2,3-Dihydro-7-diethylaminocarbonyl-9-phenyl-1H—pyrazolo[1,2-a]-indazolium chloride | 70–72° C. | 297, 369 (parent peak) |

What is claimed is:

1. A pyrazoloindazole derivative of the formula:

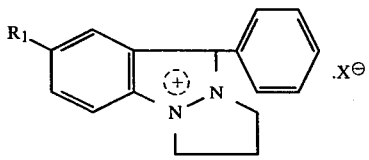

wherein $R_1$ is a cyano group, a carboxy group, a lower alkoxycarbonyl group or a group

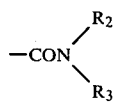

(wherein $R_2$ and $R_3$ are each a hydrogen atom, a lower alkyl group, a phenyl group which may have as a substituent a lower alkyl group having 1 to 4 carbon atoms, or when taken together with a nitrogen atom form a piperidino, piperazino, pyrrolidino or morpholino group); $X^\ominus$ is a counter ion.

2. A pyrazoloindazole derivative according to claim 1 wherein the derivative is of the formula:

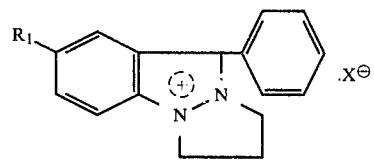

wherein $R_1$ is a cyano group, a carboxy group, an alkoxycarbonyl group having 2 to 5 carbon atoms, or group

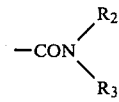

(wherein $R_2$ and $R_3$ are each a hydrogen atom, an alkyl group having 1 to 4 carbon atoms, a phenyl group which may have a lower alkyl having 1 to 4 carbon atoms or when taken together with a nitrogen atom, form piperidino, piperazino, pyrrolidino or morpholino); $X^\ominus$ is a halide ion, hydroxide ion, methanesulfonate ion, p-toluenesulfonate ion, sulfate ion, nitrate ion, carbonate ion, acetate ion, benzoate ion or a salicylate ion.

3. 2,3-Dihydro-7-cyano-9-phenyl-1H-pyrazolo[1,2-a]indazolium bromide according to claim 1.

4. 2,3-Dihydro-7-carboxy-9-phenyl-1H-pyrazolo[1,2-a]indazolium bromide according to claim 1.

5. 2,3-Dihydro-7-ethoxycarbonyl-9-phenyl-1H-pyrazolo[1,2-a]indazolium bromide according to claim 1.

6. 2,3-Dihydro-7-isobutyloxycarbonyl-9-phenyl-1H-pyrazolo[1,2-a]indazolium chloride according to claim 1.

7. 2,3-Dihydro-7-morpholinocarbonyl-9-phenyl-1H-pyrazolo[1,2-a]indazolium chloride according to claim 1.

8. 2,3-Dihydro-7-[(4-methylanilino)carbonyl]-9-phenyl-1H-pyrazolo[1,2-a]indazolium chloride according to claim 1.

9. 2,3-Dihydro-7-diethylaminocarbonyl-9-phenyl-1H-pyrazolo[1,2-a]indazolium chloride according to claim 1.

10. A pharmaceutical composition having bronchodilating activity comprising an amount sufficient to effect bronchodilation of a compound of the formula:

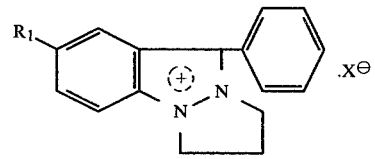

wherein $R_1$ is a cyano group, a carboxy group, a lower alkoxycarbonyl group or a group

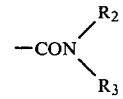

(wherein $R_2$ and $R_3$ are each a hydrogen atom, a lower alkyl group, a phenyl group which may have as a substituent a lower alkyl group having 1 to 4 carbon atoms, or when taken together with a nitrogen atom form a piperidino, piperazino, pyrrolidino or morpholino group), $X^\ominus$ is a counter ion; and a pharmaceutically acceptable carrier.

* * * * *